United States Patent
Lustiger et al.

(10) Patent No.: US 12,097,216 B2
(45) Date of Patent: Sep. 24, 2024

(54) METHOD FOR PREVENTION AND REDUCTION OF SKIN STASIS WITH COMPOSITIONS AND MATERIALS COMPRISING COPPER COMPOUNDS

(71) Applicant: MEDCU TECHNOLOGIES LTD., Herzliya (IL)

(72) Inventors: Danny Lustiger, Herzliya (IL); Gadi Borkow, Gibton (IL)

(73) Assignee: MEDCU TECHNOLOGIES LTD., Herzliya (IL)

( * ) Notice: Subject to any disclaimer, the term of this patent is extended or adjusted under 35 U.S.C. 154(b) by 651 days.

(21) Appl. No.: 17/313,429

(22) Filed: May 6, 2021

(65) Prior Publication Data
US 2021/0252049 A1 Aug. 19, 2021

Related U.S. Application Data

(63) Continuation-in-part of application No. PCT/IL2019/051161, filed on Oct. 28, 2019.

(60) Provisional application No. 62/777,409, filed on Dec. 10, 2018.

(51) Int. Cl.
*A61K 33/34* (2006.01)
*A61K 9/70* (2006.01)
*A61P 17/02* (2006.01)

(52) U.S. Cl.
CPC ............ *A61K 33/34* (2013.01); *A61K 9/7007* (2013.01); *A61P 17/02* (2018.01)

(58) Field of Classification Search
CPC ........ A61K 33/34; A61K 9/7007; A61P 17/02
See application file for complete search history.

(56) References Cited

U.S. PATENT DOCUMENTS

2008/0081077 A1  4/2008  Faryniarz et al.
2015/0209386 A1  7/2015  Gabbay
2016/0220728 A1* 8/2016  Adams .................. A61K 8/20

OTHER PUBLICATIONS

A. Borkow. "Using Copper to Improve the Well-Being of the Skin," Current Chemical Biology, 2014, 8, 89-102. (Year: 2014).*
D. Schmauss, et al. "Treatment of Secondary Burn Wound Progression in Contact Burns—A Systematic Review of Experimental Approaches," J Burn Care Res 2015; 36: e176-e189. (Year: 2015).*
Online disclosure from "Campus Cotton Club" (Kiev, Ukraine), found online at https://campuscottonclub.com/en/products/household-usage/surgical-dressing/sterile-medical-gauze-bandage-7-m-x-14-cm. (Year: 2024).*
Vorauer-uel Karola et al; "Reepithelialization of experimental scalds effected by topically applied superoxide dismutase: controlled animal studies" Wound repair and regeneration vol. 10 issue 6 pp. 366-371. (2002).
Shehan Hettiaratchy et al: "ABC of burns: Pathophysiology and types of burns" British Medical Journal pp. 1427-1429. (2004).
Nisanci M et al; "Saving the zone of stasis in burns with activated protein C: an experimental study in rats" Burns vol. 36 No. 3 pp. 397-402 (2010).
Baskaran H et al: "Poloxamer-188 improves capillary blood flow in the zone of stasis after burn injury" IEEE vol. 2. p. 775 (1999).
National PBM drug monogarph papain-urea (accuzyme) and papain-urea-chlorpophyllin copper complex sodium (panafil) 2004.
International Search Report of PCT/IL2019/051161 Completed Jan. 21, 2020; Mailed Feb. 3, 2020 5 pages.
Written Opinion of PCT/IL2019/051161 Completed Jan. 21, 2020; Mailed Feb. 3, 2020 6 pages.

* cited by examiner

*Primary Examiner* — Michael P Cohen
(74) *Attorney, Agent, or Firm* — The Roy Gross Law Firm, LLC; Roy Gross

(57) ABSTRACT

The present application relates to a method for reduction and prevention of damaged skin stasis comprising applying a material containing water-soluble or water-insoluble copper compounds to said damaged skin.

6 Claims, 13 Drawing Sheets
(6 of 13 Drawing Sheet(s) Filed in Color)

METHOD FOR PREVENTION AND REDUCTION OF SKIN STASIS WITH COMPOSITIONS AND MATERIALS COMPRISING COPPER COMPOUNDS

CROSS REFERENCE TO RELATED APPLICATIONS

This application is a continuation-in-part of PCT Patent Application No. PCT/IL2019/051161 having International filing date of Oct. 28, 2019, which claims the benefit of priority of U.S. Provisional Patent Application No. 62/777,409, filed Dec. 10, 2018, the contents of which are all incorporated herein by reference in their entirety.

TECHNICAL FIELD

The present application relates to the field of skin treatment. In particular, the present application relates to the method for reduction and prevention of skin stasis with compositions and materials comprising copper compounds.

BACKGROUND

Exposure to thermal hazard may cause injuries that constitute a significant burden, ranging from mild skin burn to life-threatening conditions that are accompanied with long-term morbidity and disability complications. In some cases, major fire disasters may strike large number of casualties at ones both in civilian and military situations. Thermal burns are inflicted by exposure of the skin to high temperature often by hot liquids, steam or flames. The severity of burn injury is determined by temperature, time of exposure and exposure area. Severe burns cause extreme physiological burden on the patient for a prolonged period of time.

Douglas MacG. Jackson in "*The diagnosis of the depth of burning*", The British Journal of Surgery 40 (1953), pp. 588-596, mentioned that the local endogenous response of a skin to thermal burn can be characterised as resulting in three different injury patterns of varying degrees depending on the severity of the burn and the cause. The point of maximum irreversible damage is referred to as zone of coagulation since there occurs tissue loss due the coagulation of the skin proteins. The zone around the coagulation zone, referred as the zone of stasis, is characterised by decreased tissue perfusion, and depending on the severity of the burn, hypotension, infection, inflammation and/or oedema may lead this zone into an area of complete tissue loss.

The zone of stasis is formed around the coagulation zone following skin burning and is characterized by its unique potential for salvation. The cells in this zone, may die or survive, depending on the severity of the burn and therefore are target for the local treatments of burns. Their low survival rate is consistent with decreased tissue perfusion, hypotension, infection, inflammation and/or edema, resulting in a significant increase in the wound size following burning.

Shehan Hettiaratchy and Peter Dziewulski in "*Pathophysiology and types of burns*", BMJ 328 (7453) (2004), pp. 1427-1429, showed that around the zone of sepsis, a zone of hyperaemia is characterised by increased perfusion that will invariably recover unless there is severe sepsis or prolonged hypoperfusion. The middle zone of stasis, while initially viable, following the reduced perfusion dies and the initial size of the wound deepens and widens.

Following severe skin injury of above of 30% of total body surface area, release of cytokines and other inflammatory mediators at the site of injury, may lead to several systemic responses that can be detrimental. These include a) significant increase in capillary permeability, leading to loss of intravascular proteins and fluids into the interstitial compartment, peripheral and splanchnic vasoconstriction and myocardial contractility decrease. These cardiovascular changes coupled with fluid loss from the burn wound, result in systemic hypotension and end organ hypoperfusion; b) bronchoconstriction, and potentially respiratory distress syndrome; c) increase of the basal metabolic rate by up to three times its original rate; and d) non-specific cell mediated and humoral immune responses down regulation.

Ara A. Salibian et al in "*Current concepts on burn wound conversion. A review of recent advances in understanding the secondary progressions of burns.*", Burns 42(5) (2016), pp. 1025-1035, suggested that the stasis zone is a therapeutically critical section of burn surface that can be salvaged. Prevention of the progression and expansion of the wound injury into larger and deeper areas may have important local and systemic consequences that may significantly decrease complications and morbidity. Thus, developing therapies that can halt the further deterioration of the zone of stasis following wound burn injury can be an important modality of burn wound treatment after patient stabilization and prior to skin reconstruction.

Copper is an essential trace element involved in many cellular, metabolic and physiological processes in almost all body tissues, and needed for the normal function of almost all body tissues, including the skin. Neena Philips et al in "*Stimulation of cell proliferation and expression of matrix-metalloproteinase-1 and interluekin-8 genes in dermal fibroblasts by copper*", Connective Tissue Research 51(3) (2010), pp. 224-229, demonstrated that copper is capable of stimulating dermal fibroblasts proliferation in skin. Further, Neena Philips et al in "*Beneficial regulation of fibrillar collagens, heat shock protein-47, elastin fiber components, transforming growth factor-beta 1, vascular endothelial growth factor and oxidative stress effects by copper in dermal fibroblasts*", Connective Tissue Research 53(5) (2012), pp. 373-378, showed that copper in the skin enhances production and secretion of different collagen and elastin types by fibroblasts.

Also, it has been shown that copper is capable of stabilising the skin extracellular matrix once formed, serves as a cofactor of superoxide dismutase, an antioxidant enzyme present in the skin, important for protection against free radicals, serves as a cofactor of lysyl oxidase, an enzyme that catalyses lysine-derived crosslinks in the skin extracellular matrix, and inhibits cellular oxidative effects such as membrane damage and lipid peroxidation. However, the surprising effect of copper ions on reducing stasis of skin burns has not been known yet. It has now been discovered by the present inventors and constitutes the basis of the present invention.

SUMMARY

The present application describes embodiments of a method for reduction and prevention of damaged skin stasis comprising applying a material containing water-soluble or water-insoluble copper compounds to said damaged skin. In other embodiments, said material is a woven or non-woven fabric, a foam, a knit fabric, or any type of fabric that is used to make wound dressings, plasters, gauze or the like. This material is impregnated with about 0.1-10% w/w water-insoluble copper particles or coated with about 0.1-10% w/w water-insoluble copper particles.

In a further embodiment, said water-insoluble copper particles are specifically cuprous iodide (CuI) or cuprous oxide ($Cu_2O$) particles. The exemplary material of the embodiments is a woven fabric impregnated or coated with approximately 0.1-10% w/w cuprous iodide (CuI) particles or a sterile wound dressing impregnated or coated with approximately 0.1-10% w/w $Cu_2O$ particles.

In yet further embodiment, said composition is in a form of a liquid spray or ointment containing water-soluble copper compounds. The exemplary water-soluble copper compounds of the embodiments are cupric sulphate ($CuSO_4$) or cupric chloride ($CuCl_2$).

In another embodiment, said material is in a form of a polymeric film, fibre, filament or sheath. The exemplary polymeric film of the embodiments comprise polymers selected from the group of polyester, polypropylene, polyethylene, Nylon 66, Nylon 6, polyamide and polyurethane. The polymeric material of the present embodiment comprises water-insoluble particles of copper compounds in a powdered form, embedded directly inside said film, fibre, filament or sheath, wherein a portion of said particles being exposed and protruding from the surface of the film, fibre, filament or sheath, or said polymeric material is coated with water-soluble copper compounds or water-insoluble particles of copper compounds. The exemplary water-insoluble particles of copper compounds of the present embodiment are selected from cuprous iodide, cuprous oxide and cupric oxide, or combinations thereof, in a powdered form.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Disclosed embodiments will be understood and appreciated more fully from the following detailed description taken in conjunction with the appended figures.

The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

DETAILED DESCRIPTION

Figure 1A:
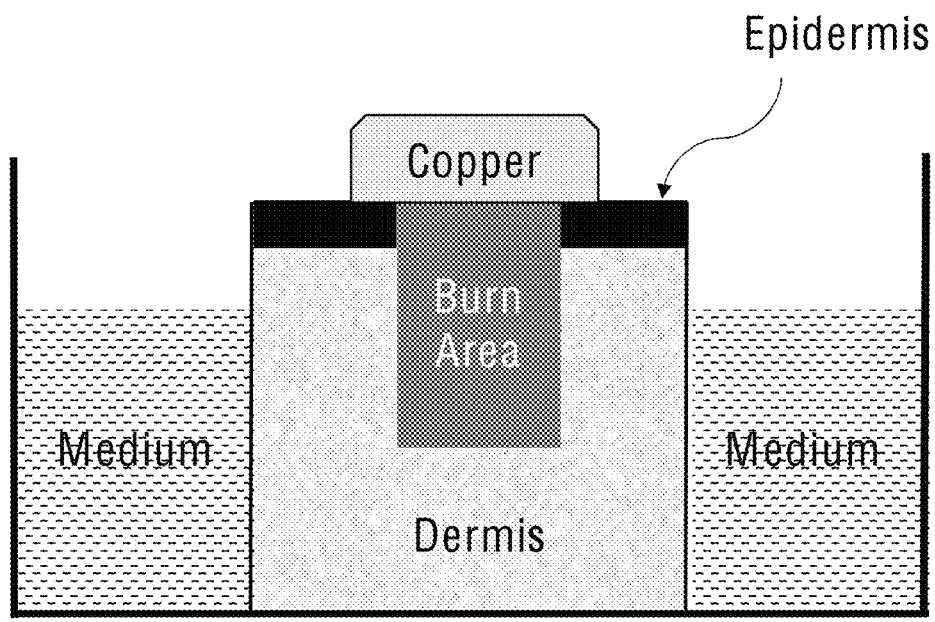
FIGS. 1a and 1b schematically show a side view and a top view, respectively, of the ex-vivo explant model of the present invention.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a material comprising x and z" should not be limited to materials consisting only of compounds x and z. Also, the scope of the expression "a method comprising the steps x and z" should not be limited to methods consisting only of these steps.

Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The present application provides a method for prevention and reduction of damaged skin stasis comprising applying a composition or material comprising copper compounds to said damaged skin. Said composition can be an aqueous solution of water-soluble copper compounds or suspension of water-insoluble copper compounds in water, in a solvent or in a mixture thereof. Said composition can be, for example, in a form of a liquid, spray, gel, ointment or powder. Said material can be a woven or non-woven fabric, a foam, a knit fabric, or any type of fabric that is used to make wound dressings, plasters, gauze or the like.

In some embodiments, the material is impregnated with about 0.1-10% water-insoluble copper particles. In other embodiments, the material is coated with about 0.1-10% water-insoluble copper particles. Examples of the water-insoluble copper particles used in the material of the present embodiments are cuprous iodide (CuI) and cuprous oxide ($Cu_2O$) particles. In a specific embodiment this material is a sterile wound dressing impregnated with approximately 1-3% weight/weight water-insoluble $Cu_2O$ particles. In a specific embodiment, the composition is in a form of a liquid spray or ointment containing water-soluble copper compounds, for example cupric sulphate ($CuSO_4$) or cupric chloride ($CuCl_2$).

In a particular embodiment, the material comprising copper compounds is a polymeric film, fibre, filament or sheath. The polymers used in the polymeric film is selected from polyester, polypropylene, polyethylene, Nylon 66, Nylon 6, polyamide and polyurethane. In a specific embodiment, this polymeric material comprises microscopic water-insoluble particles of copper compounds, such as cuprous oxide ($Cu_2O$) and/or cupric oxide (CuO) in a powdered form, embedded directly inside said film, fibre, filament or sheath, wherein a portion of said particles being exposed and protruding from the surface of the film, fibre, filament or sheath. In yet further specific embodiment, said polymeric material is coated with the water-insoluble particles of copper compounds. The material being embedded or coated with the copper compounds is capable of releasing Cu(I) ions, Cu(II) ions or combination thereof upon contact with the damaged skin.

EXAMPLES

Example 1

Ex-Vivo Model

Human skin was obtained from healthy donors undergoing abdominal dermolipectomy after receiving informed consent. A 0.5 mm split-thickness skin graft was harvested using a dermatome (Aesculap AG & Co. KG, Tuttlingen, Germany) and was cut into 1 $cm^2$ pieces. Round burn wounds of with a diameter of 25 mm were inflicted in the 0.7 $cm^2$ skin pieces by exposure to a soldering iron (95° C., 2 Sec). Triplicate pieces were kept intact as naïve controls. The injured and intact skin samples were placed dermis down on a stainless-steel grid and cultured at the air-liquid interface at 37° C. with 5% CO2 in Dulbecco's Modified Eagle's Medium (DMEM), 10% fetal calf serum (Biological Industries, Beit Ha'emek, Israel), and penicillin/streptomycin (100 IU/mL penicillin, 100 mg/mL streptomycin; Invitrogen). Culture medium was refreshed twice a week. The explants were cultured up to 27 days after wounding. Each individual experiment was performed with skin explants obtained from the same individual and the experiments were repeated at least three times.

Figure 1B:
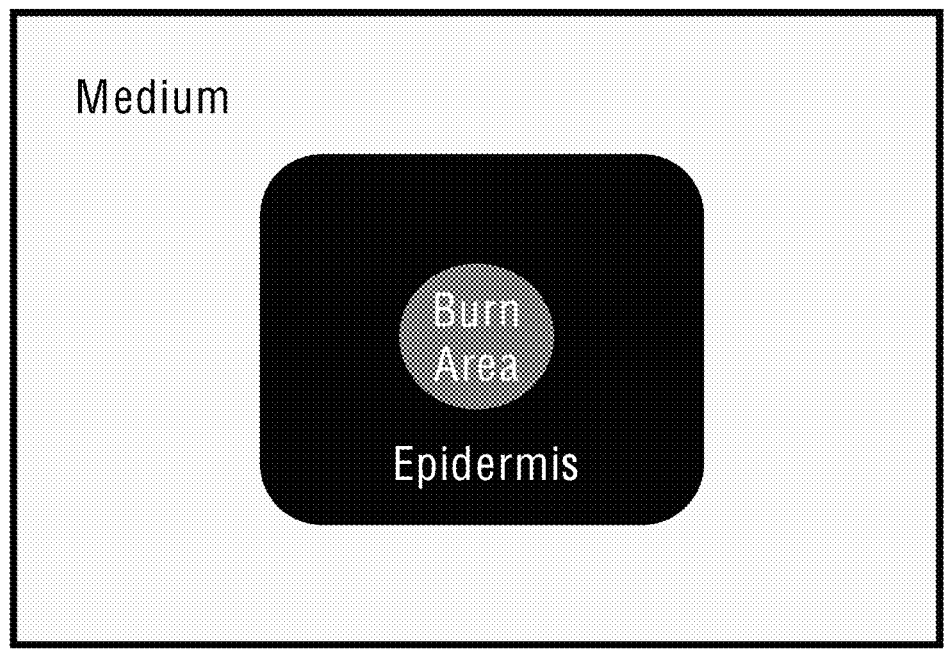

Reference is now made to FIGS. 1a and 1b schematically showing a side view and a top view, respectively, of this ex-vivo explant model. The skin explants are placed dermis down on a stainless-steel grid. Culture media is added to the bottom of the well, without reaching the epidermal layer, which is exposed to the air. 3 μL of saline only or containing different concentrations of the copper solutions are carefully added on top of the burned area and around it making sure it does not reach the culture media in the bottom of the well.

Copper Source and Application on the Skin Explants

As a source of copper ions, two items were used: woven fabric impregnated with about 1% copper iodide microparticles (Cupron Inc., USA) and sterile wound dressings impregnated with about 1.2% weight/weight cuprous oxide micro-particles (MedCu Technologies Ltd., Israel).

Prior to use, the copper iodide impregnated fabric was sterilised using UV light. 0.84 grams of the copper iodide impregnated fabrics and 3.6 grams of the cuprous oxide impregnated wound dressings were immersed in 25 ml of 0.9% saline overnight at 37° C. The resulting concentration of copper ions in the medium was determined by using Aquachek™ copper ions test strips (Hach Company, USA), and these solutions served as copper ions stock solutions, identified hereafter as copper iodide solution and cuprous oxide solution, respectively, to clearly identify the copper ion source.

From the stock solutions, solutions of 0.02 µM or 1 µM of copper ions were prepared in saline. Three µL of saline only, 0.02 µM or 1 µM copper solutions were then added on Day 0 and then after every two days onto the skin explants on top of the burn area and the epidermis around the burn area making sure that they do not reach the medium in the chamber but stay on the air interface on top of the skin. Each control and treatment were performed in at least three replicate explants.

Measurement of Viability

To assess the cell viability throughout the culture period a 3-(4,5-dimethylthiazol-2-yl)-2,5-diphenyltetrazolium bromide (MTT) assay was performed at different days after wounding as follows:

Bioassay

During harvesting time points, the spent medium from all Test Groups was collected and centrifuged at 1500×g for 5 minutes to remove particulates. Media were kept at −80° C. until use. The secretion levels of IL-6, IL-8 and TGF-β were measured by commercial Enzyme-Linked Immunosorbent Assay (ELISA) kits according to manufacturer instructions (Biolegend, San Diego, CA). Briefly, plates were coated for 24 hours prior to assay with a specific anti-human capture antibody. At the day of the assay, coated plates were incubated with samples, followed by washes for unbound molecules. Then additional detection antibody was added and detected by Avidin-HRP solution. Finally, wells were incubated with a substrate solution, while absorbance was measured at 570 nm.

Statistical Analysis

Statistical analysis was performed using SigmaPlot 12.0 software. The experimental values presented as average of three replicates and standard errors of the mean (SEM) are provided. Significant differences between values were analysed using the unpaired t-test, while significant results are for p<0.05.

Experimental Results

Figure 2A:
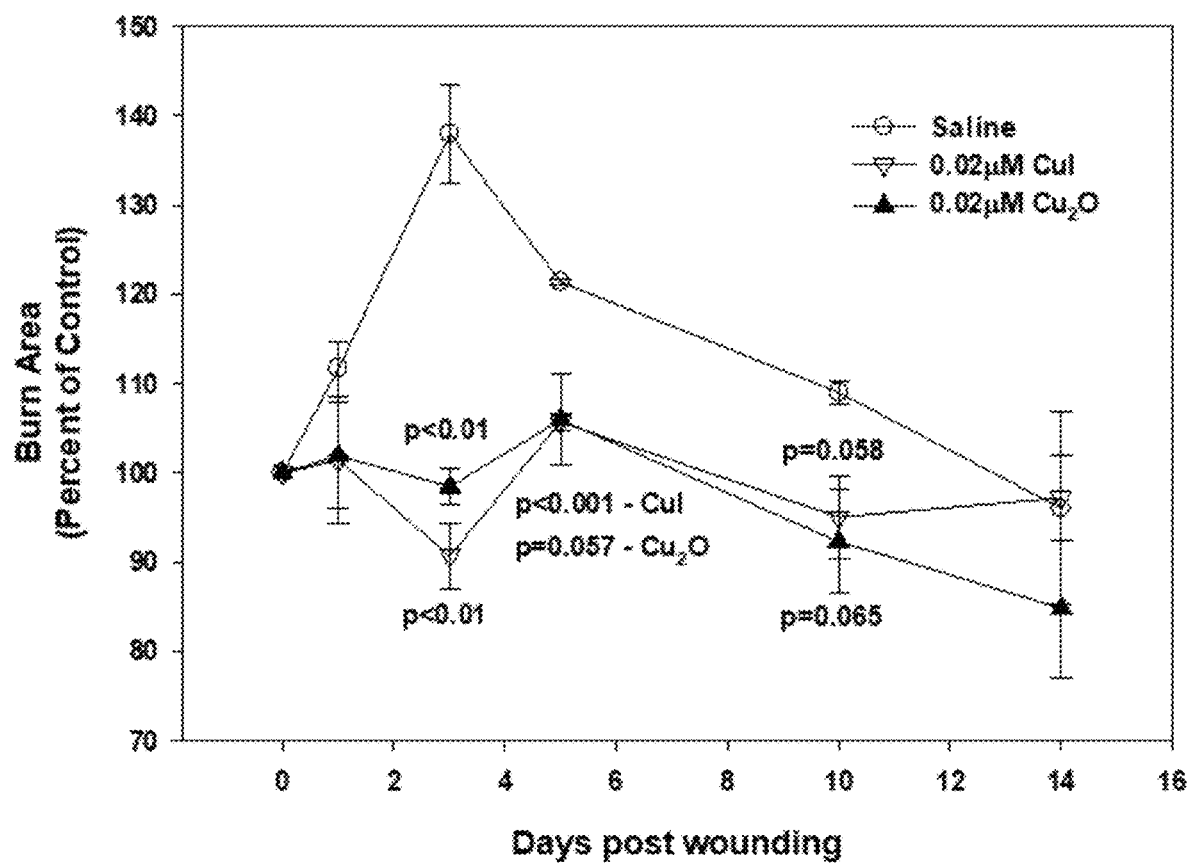
FIG. 2a shows the experimentally generated graph of burn area of the explants at different days following wounding.
Figure 2B:
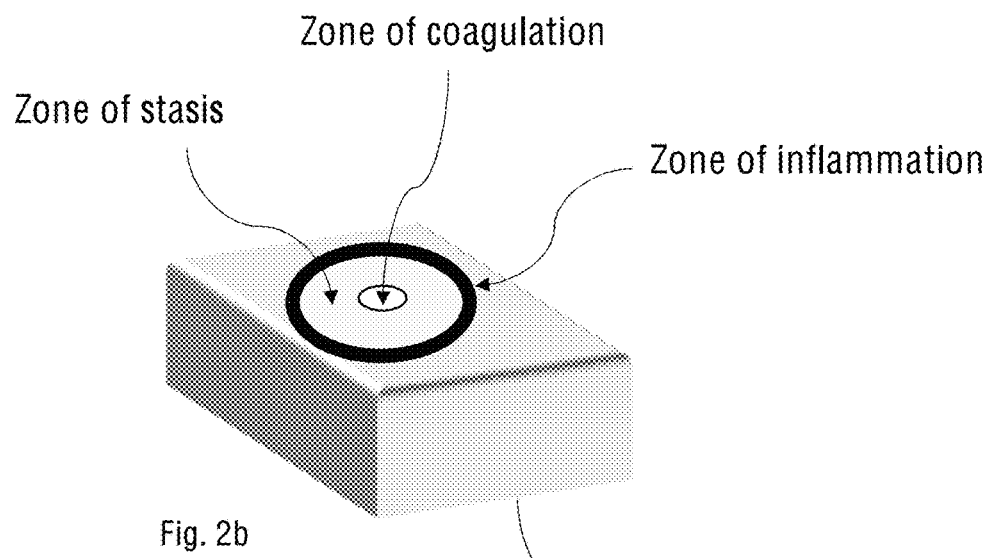
FIG. 2b schematically shows the explant with the burn area having the zone of stasis.
Figure 2C:
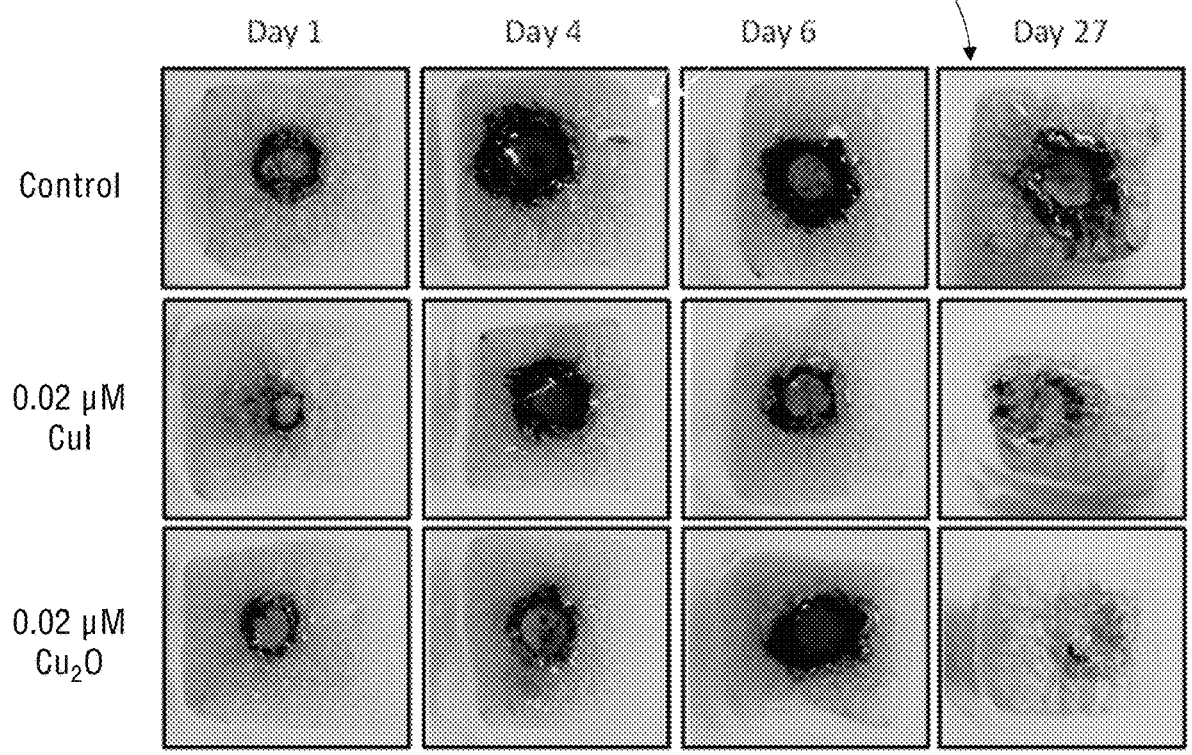
FIG. 2c shows the photographs of the explants treated with saline only (Control) and with copper ions (0.02 µM of cuprous iodide and 0.02 µM cuprous oxide).
Figure 5A:
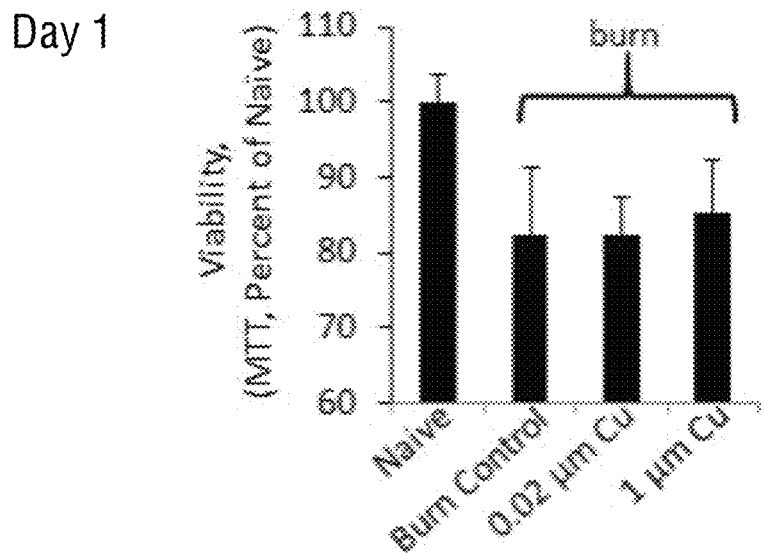
FIGS. 5a-5b shows viability of the epidermis after 1 and 5 days, following burn infliction, determined by MTT. The results are presented as means±standard error, of three replicates in a representative experiment performed with skin explants obtained from the same donor.
Figure 5B:
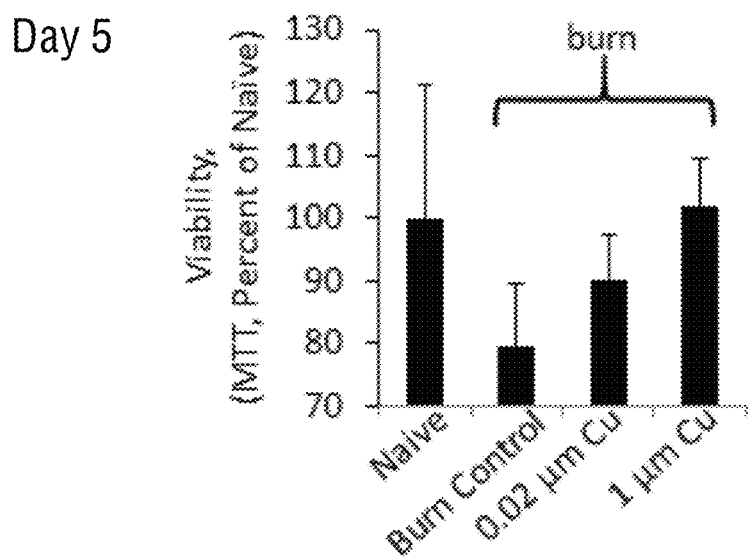

Reference is now made to FIG. 2a showing the experimentally generated graph of burn area of the explants at different days following wounding. The p values between the treatment groups and the untreated Burn Control groups is shown. FIG. 2b schematically shows the explant with the burn area having the zone of stasis. FIG. 2c shows the actual pictures of the explants treated with saline only (Control) or with 0.02 µM copper ions. The differences in size of the wounds between the treatments, especially in the zone of stasis, is clearly visible in FIG. 2c. When burned, skin explants were treated with 0.02 µM or 1 µM of copper ions, the viability of the treated pieces remained similar to the untreated pieces after 1 day. However, following 5 days since the burn was inflicted, a trend of increased viability was observed, depending on the copper concentration, though the differences were not statistically significant. FIGS. 5a and 5b shows viability of the epidermis after 1 and 5 days, respectively following burn infliction, as determined by MTT. The results are presented as means values±standard error, of three replicates in a representative experiment performed with skin explants obtained from the same donor.

As can be seen in FIG. 2a, the burn-wounds treated by saline only increased significantly becoming almost 40% larger three days following wounding and then started to decrease gradually reaching the initial wound size 14 days following wounding. In contrast, the size of the wounds treated with 0.02 µM copper ions obtained from the copper iodide or cuprous oxide particles almost did not change. The size of the wounds treated with saline containing 0.02 µM copper ions was statistically smaller than the wounds treated with saline only three days following wounding and similarly smaller wounds were measured in the copper-treated explants 5- and 10-days following wounding. As clearly seen in FIG. 2c, the skin zone which did not increase in size following burning in the copper-treated explants is the zone of stasis.

Figure 3A:
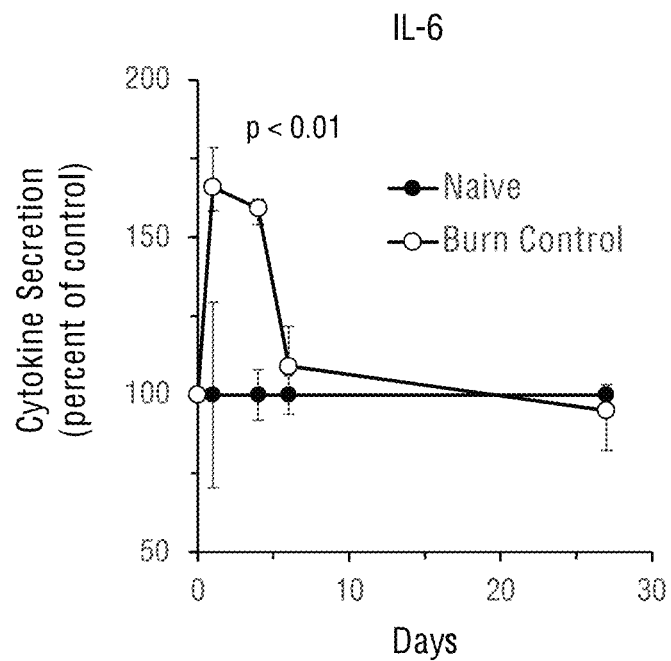
FIGS. 3a, 3c and 3e show the cytokine expression in burn-induced inflammation in human ex vivo skin and comparison between the IL-6, IL-8 and TGF-β kinetic secretion, respectively, in the untreated skin explants (Naïve Controls) and the wounded skin explants (Burn Controls) following wounding. Results are presented as percent of controls and normalised each day to Naïve control. The p values of a t-test between the cytokine expressions per a particular day following wounding are shown.

In order to further understand how addition of copper ions affected the skin explants, the amounts of Interleukin 6 (IL-6), Interleukin 8 (IL-8) and transforming growth factor beta (TGF-ß) found in the medium of the various treated explants were determined. FIGS. 3a, 3c and 3e show the cytokine expression in burn-induced inflammation in human ex vivo skin and comparison between the IL-6, IL-8 and TGF-β secretion by the untreated skin explants (Naïve Controls) and the wounded skin explants (Burn Controls) following wounding. In these figures, the p values of a t-test between the cytokine expressions per a particular day following wounding are shown. Measurements were normalized to amount of cytokine secreted from normal skin and are presented as percent of Naïve control.

Figure 3B:
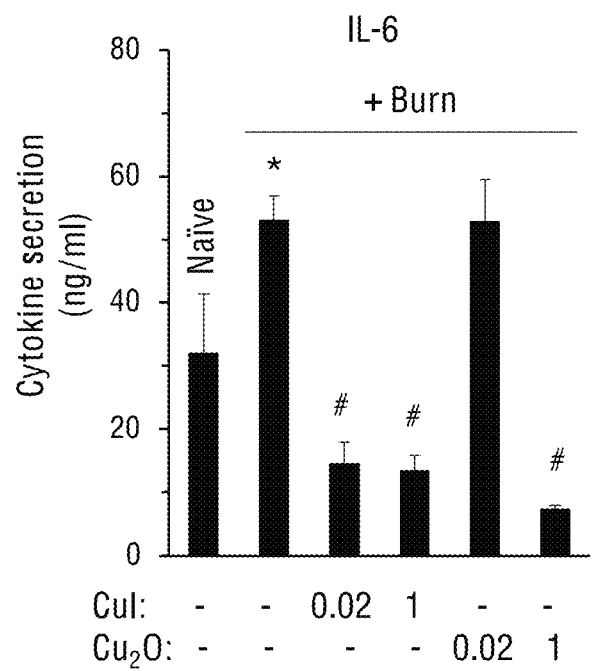
FIGS. 3b, 3d and 3f show the effect of addition of copper ions (0.02 µM or 1 µM) on secretion of IL-6, IL-8 and TGF-β, respectively, as compared to Naïve Controls and Burn Controls on Day 4 (FIGS. 3b and 3d) and on Day 6 (FIG. 3f) after wounding.
Figure 3C:
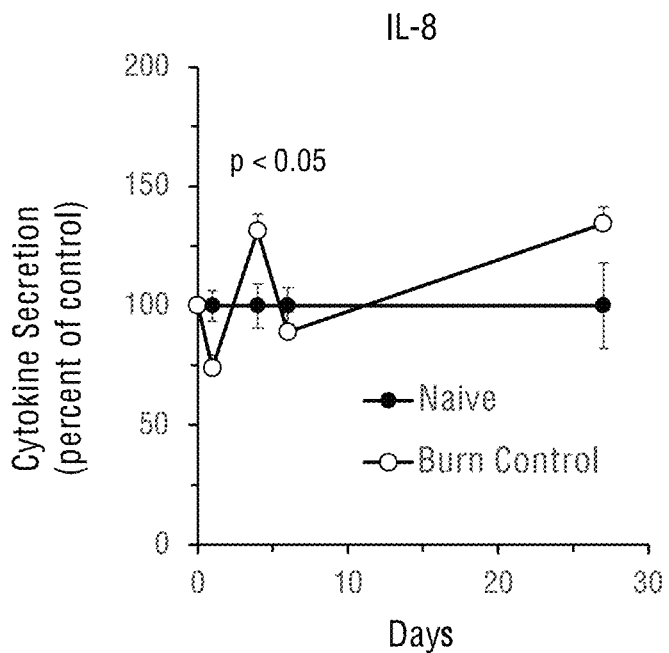
Figure 3D:
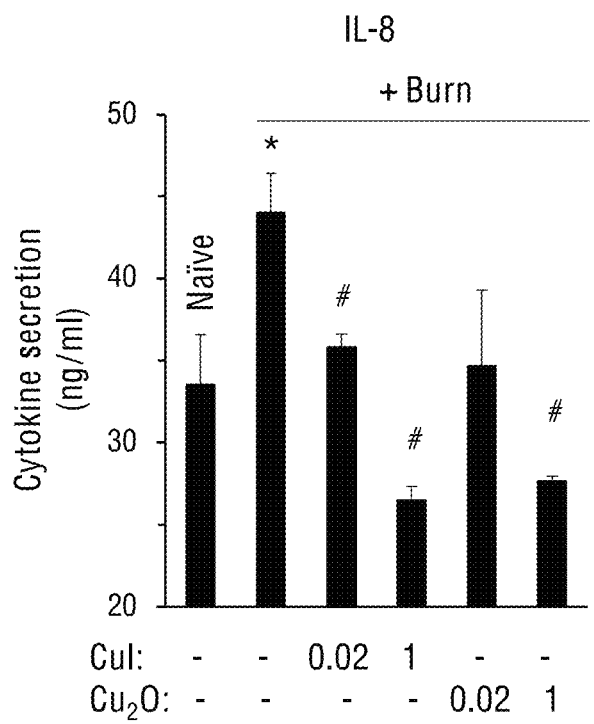
Figure 3E:
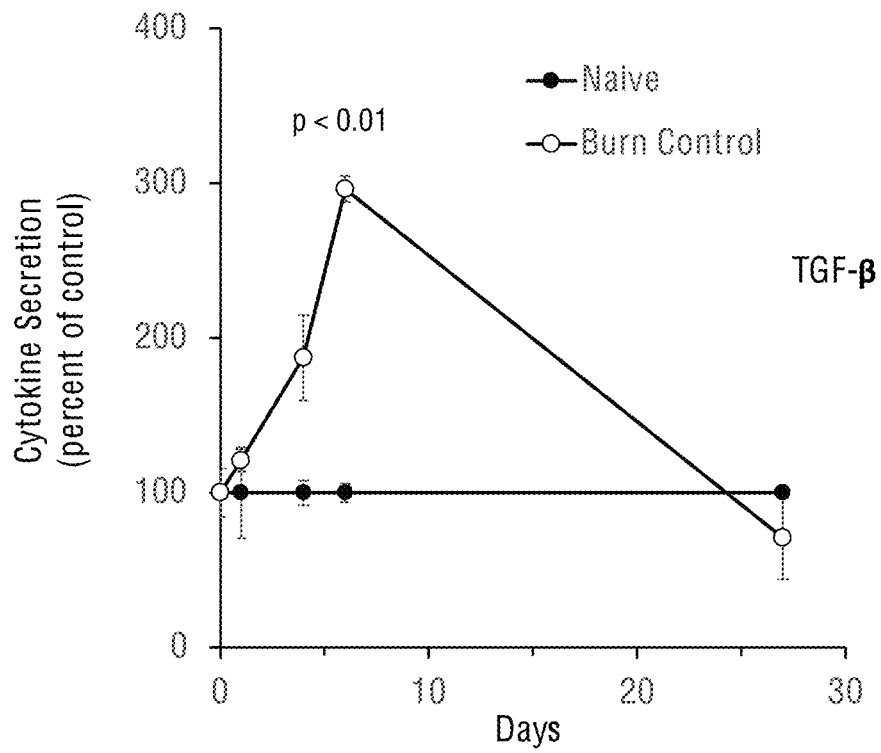
Figure 3F:
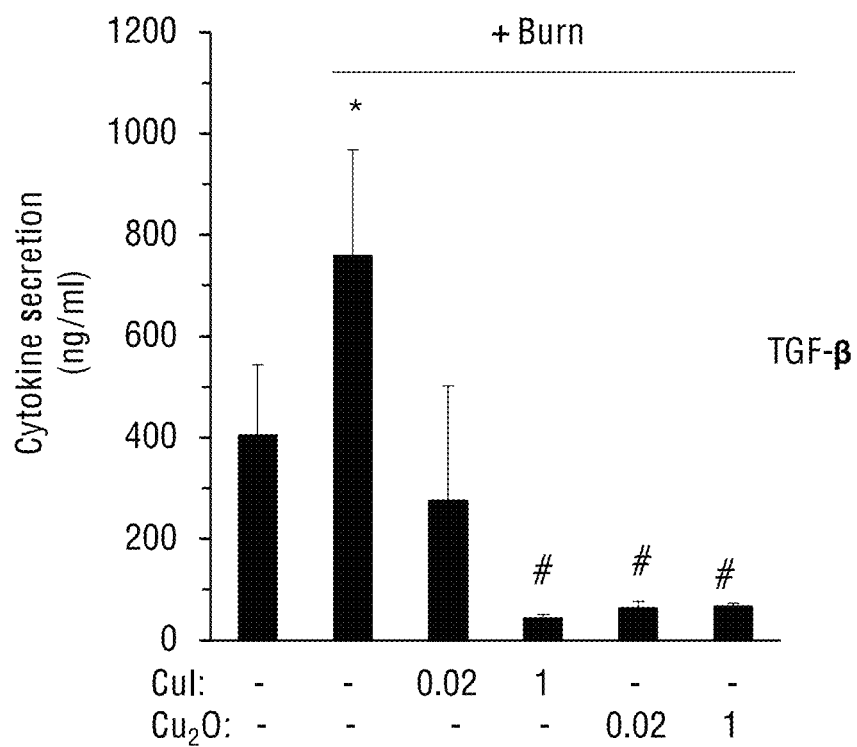

Reference is also made to FIGS. 3b, 3d and 3f showing the effect of addition of copper ions (0.02 µM or 1 µM) on secretion of IL-6, IL-8 and TGF-β, respectively, as compared to Naïve Controls and Burn Controls on Day 4 (treated with saline only) (FIGS. 3b and 3d) and on Day 6 (FIG. 3f) after wounding. In the graphs, the star sign "*" indicates the statistically significant difference as compared to the Naïve Controls, while the net sign "#" indicates the statistically significant difference as compared to the untreated (treated with saline only) Burn Controls.

As seen in FIG. 3a, in the Burn Controls, there was a clear increase in IL-6 secretion after one day and four days following wounding as compared to the Naïve Controls. Addition of 0.02 µM or 1 µM of copper ions from the CuI stock solution and of 1 µM of copper ions from the $Cu_2O$ stock solution to the burned explants abolished the increase in IL-6 secretion by the explants, and actually resulted in even reduced IL-6 secretion as compared to the IL-6 secretion by the Naïve Controls (see FIG. 3b). After Day 4, there were no significant differences in IL-6 levels between Burn Control samples and the copper treated samples.

Similarly, the statistically significant increase of IL-8 and TGF-β in the Burn Controls as compared to the Naïve Controls on Day 4 after wounding (see FIGS. 3c and 3e, respectively) was significantly attenuated or abolished when the burn wounds were exposed to 0.02 µM or 1 µM of copper ions from both copper sources (see FIGS. 3d and 3f). Indeed, these figures clearly shows that on Day 1, the amount of IL-8 secreted by the samples treated with copper containing saline did not differ significantly than the amounts secreted by the Burn control samples, which were all statistically significantly lower that the IL-8 secretions by Naïve controls. In contrast, IL-8 levels, which were elevated in the Burn controls as compared to the Naïve Controls (see FIGS. 3c and 3d) at Day 4, were attenuated by the addition of the copper ions, being similar to the IL-8 levels secreted by the Naïve controls (FIG. 3d).

Similarly, the levels of TGF-β, which increased gradually during the first days after burning, reaching a peak on Day 6, (see FIGS. 3e and 3f), were significantly inhibited by the presence of the copper ions in the solution on Day 4 (FIG. 3f). On the other examined days, there were no statistically significant differences between the TGF-secretion of the Burn control samples and the copper treated samples.

Figure 4A:
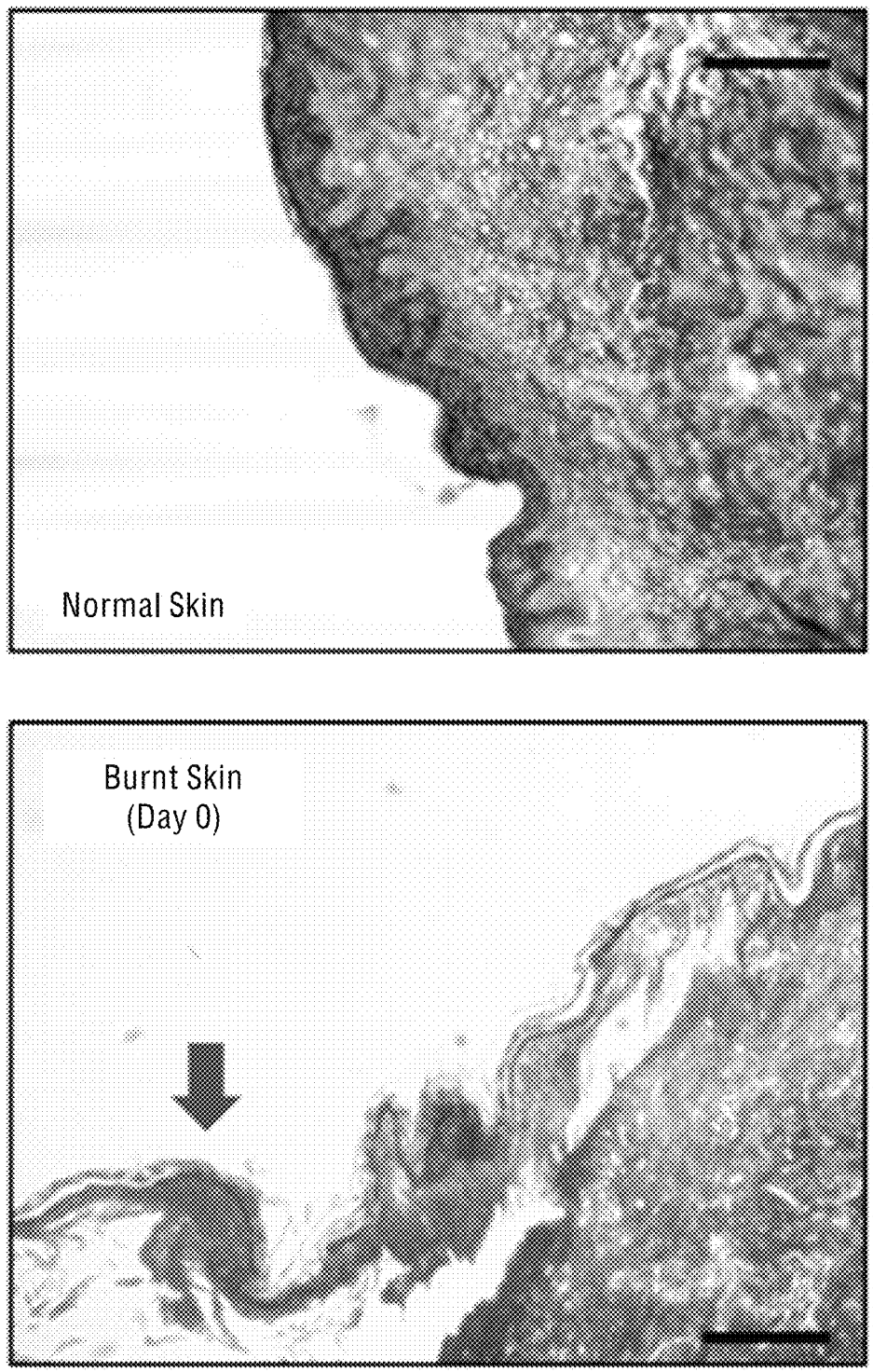
FIGS. 4a-4c show histologically stained samples with Masson's trichrome staining of skin tissue explants at Days 0, 6 and 27 after wounding, respectively.
Figure 4B:
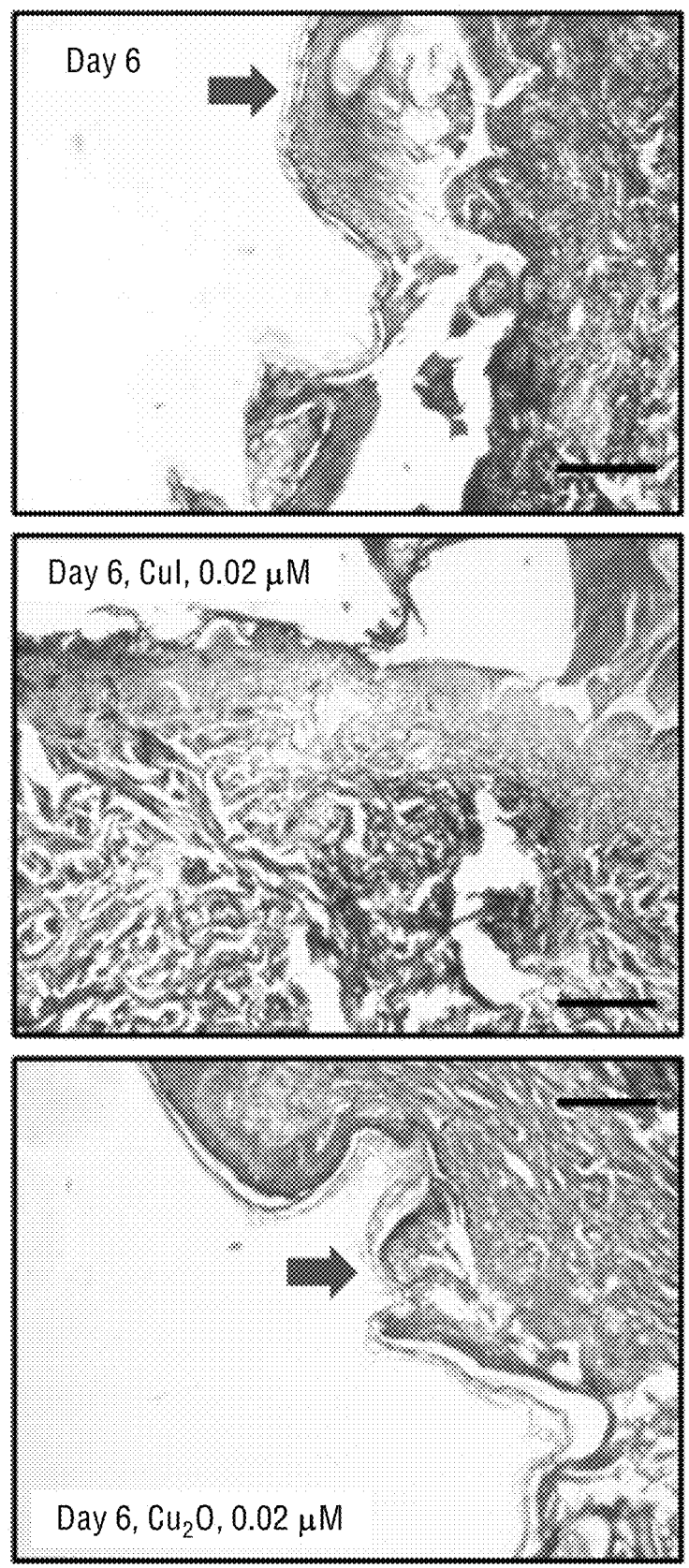
Figure 4C:
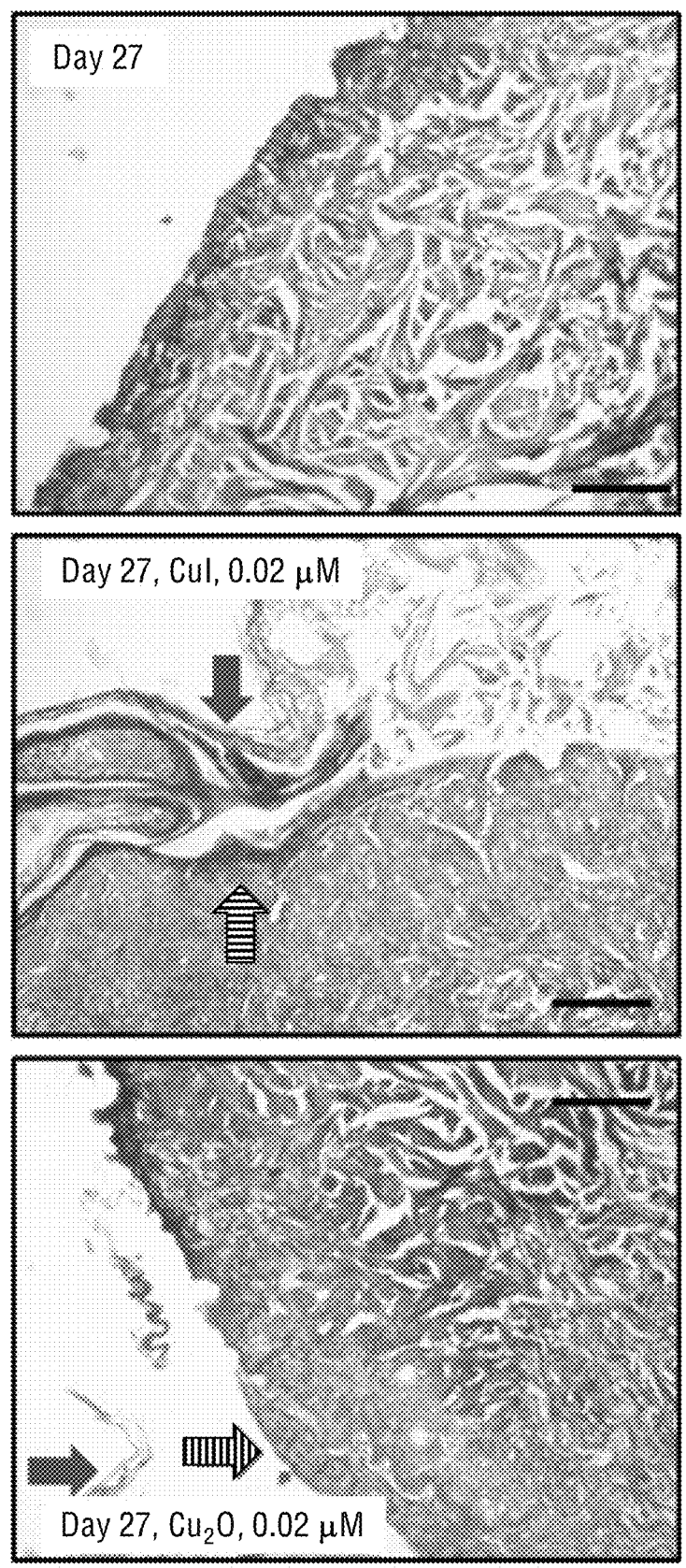

Reference is now made to FIGS. 4a-4c showing histologically stained samples of skin tissue stained with Masson's trichrome staining at Days 0, 6 and 27, respectively, which enables to detect both epidermal and dermal changes by staining cells in red and collagen fibers in blue.

In normal tissue, healthy epidermal layer was attached to the dermis, whereas immediately after burning, the epidermis was detached and the damaged tissue is indicated by the gray arrow (FIG. 4a, upper panel showing normal healthy skin). At Day 0 (see FIG. 4a, lower panel), burns were inflicted on skin explants. FIG. 4a, lower image, shows damaged skin tissue, immediately following the burn infliction. Epidermis is detached from the dermis (as indicated with the solid arrow).

At Day 6 (FIG. 4b) and Day 27 (FIG. 4c), old, separated epidermis, following the burn infliction, without or with copper ion treatments, is indicated with the solid arrow. Re-epithelisation is noted on Day 27 (see FIG. 4c) only upon copper-ion treatments, as indicated by the stripe arrows, but not in the control samples. Samples were fixated on indicated time points and histologically stained by Masson's trichrome dye. Histological analyses revealed that only in the copper-ion treated samples clear re-epithelisation occurred (see FIG. 4c, stripe arrows). In addition, greater collagen stain is observed in the copper ions treated samples (see FIG. 4c).

Example 2

Method

Skin was obtained from 35-65-year-old healthy patients undergoing abdominoplasty surgery. The patient's under general anesthesia, went standard or circumferential abdominoplasty. After excision of the excess skin, the subcutaneous fat was removed using sterile technique. The defatted full-thickness skin was submerged in culture medium and transferred to the laboratory. The skin was cut into 8×8 mm squares by costume made apparatus. Round 0.8 mm diameter burn wounds were inflicted on the skin explants by exposure to a soldering iron (200° C., 10 Sec).

The injured (burnt) and control intact skin samples were placed dermis down and kept at the air-liquid interface at 37° C. with 5% $CO_2$ in Dulbecco's Modified Eagle's Medium supplemented with 100 IU/mL penicillin and 100 mg/mL streptomycin and 10% serum (Biological Industries, Beit Ha'emek, Israel). Culture medium was refreshed every 48 hours, i.e. immediately following injury and then again, every 48 hours, saline only or containing 0.02 µM or 1 µM copper ions were added onto the skin explant burn wounds. The explants were cultured up to 27 days after wounding.

Each individual experiment was performed with skin explants obtained from the same donor. At least three independent experiments from three different donors were performed for each parameter studied. A sketch of the model is presented in FIGS. 1a-1b.

Copper Source and Application on the Skin Explants

Copper source and application on the skin explants are the same as in Example 1 above.

Measuring Wound Area

Pictures of burns were captured using Motic® Moticam 5+ camera at designated time points. Wound area was measured using ImageJ software suit. The obtained results are presented as means±SEM.

Measurement of Viability

To assess the cell viability throughout the culture period a 3-(4,5-dimethylthiazol-2-yl)-2,5-diphenyltetrazolium bromide (MTT) assay was performed 1, 3, 5, 10, 14, 21 and 27 days, following wounding, as follows: skin explants were incubated for 60 sec in pre-warmed PBS (56° C.). Then the epidermis layer of each replicate was separated from the dermis by grabbing the tissue edge with tweezers and peeling the epidermis off using a scalpel. Epidermal pieces were transferred to 96 well-plate, each well contains 150 µl MTT (Sigma, 0.5 mg/ml) and incubated for 1 hour at 37° C. and reduced light conditions. Then, the epidermis pieces were transferred to a new 96 well-plate containing 150 µl of isopropanol. Plates were placed for 5 min, 200 rpm in a plate shaker (MRC, Beijing, China). Following incubation, epidermis sections were removed, and absorbance was measured at 570 nm in Tecan plate reader (Tecan Group Ltd. Switzerland).

Bioassay

Bioassay was the same as in Example 1 above.

Histology and Immunohistochemistry

At indicated harvesting time points, skin explants were fixed with 4% formaldehyde for 1 hour at room temperature. Then, the samples were washed twice with PBS and kept at 70% ethanol at 2-8° C. until use. Following dehydration in gradual increasing concentrations of ethanol and embedment, paraffin sections (8 µm) were prepared, pasted on slides and either stained with haematoxylin and eosin (H&E) or Masson trichrome stain, according to the manufacturer specification (Sigma-Aldrich) followed by mounting with DPX mountant (Sigma, Israel).

Immunostaining with Rabbit-anti Ki67 (Abcam, UK) was performed following rehydration, blocking in 2% BSA in PBS for 20 mins, for 2 hours, followed by exposure to Goat Anti-Rabbit IgG H&L (HRP) for one hour and detection by DAB substrate (Abcam, UK). Washes were then performed in 0.025% Tween/PBS. Counterstain was performed with haematoxylin (Sigma, Israel). Images were captured using Zeiss® PrimoVert microscope connected to Motic® Moticam 5+ camera.

Statistical Analysis

Statistical analysis was the same as in Example 1 above.

Experimental Results

Epidermal Viability

The exposure of healthy, non-burned, skin explants to 0.02 µM or 1 µM of copper ions obtained from copper oxide or copper iodide impregnated fabrics, did not significantly affect epidermal viability compared to vehicle (saline) treated controls during ex-vivo explants culture and were found to be safe for use in the ex-vivo experimental system (data not shown). When examining viability of the epidermal layer upon burn inflictions following 1 and 5 days, the viability of the epidermis was reduced in an average of 20% compared to naïve, non-burned pieces, based on the average of three independent experiments, from three different donors.

When burned skin explants were treated with 0.02 µM or 1 µM of copper ions, the viability of the treated pieces remained similar to the untreated pieces after 1 day. However, following 5 days since the burn was inflicted, a trend of increased viability was observed (which is in accordance with the decreased damage or death of the cells in the zone of stasis), depending on the copper concentration, though the differences were not statistically significant. As mentioned above in the first example, FIGS. 5a and 5b show viability of the epidermis after 1 and 5 days, respectively following burn infliction was determined by MTT. The results are presented as means values±standard error, of three replicates in a representative experiment performed with skin explants obtained from the same donor.

Wound Area Measurement

In order to evaluate the size of burns, pictures of the skin explants were taken and burns size were measured. Three independent experiments from three different donors were performed. These are actually the same measurements of the burn wound size shown in FIGS. 2a-2c. As can be seen in FIG. 2a, which shows a representative experiment on quantitation of the burn size (area) at different days following burn infliction. In FIG. 2a, the p values between the treatment groups and the untreated Burn Control groups per a given day are shown. As can be seen in FIG. 2a, the size of the burn-wounds treated by saline only increased significantly following wounding, becoming almost 40% larger than the initial size after three days of wounding. This is attributed to the zone of stasis.

Following aggravation, the size of burn started to decrease gradually reaching the initial wound size 14 days following wounding. FIG. 2b shows representative pictures of the explants treated with saline only (Control), or 0.02 µM copper ions, showing clear differences in the size of the wounds between the treatments, especially in the zone of stasis as clearly visible in FIG. 2c.

Thus, the size of the wounds treated with 0.02 µM copper ions obtained from either copper iodide or cuprous oxide particles did not change significantly following wounding. It remained statistically smaller than the wounds which are treated with saline only at three days following wounding and similarly smaller wounds were measured in the copper-treated explants at days 5 and 10 following wounding. As shown in FIG. 2a and clearly seen in FIG. 2c for different experiments, the main zone, which did not increase following burning in the copper-treated explants, was the zone of stasis. The significant effect of the copper ions, on the prevention in the increase of the wound size following the burning of the skin explants, were observed in all three experiments performed.

Measurement of Cytokines IL-6, IL-8 and TGF-β1

Measurements of cytokines was the same as in Example 1.

Histological Examination

Figure 6A:
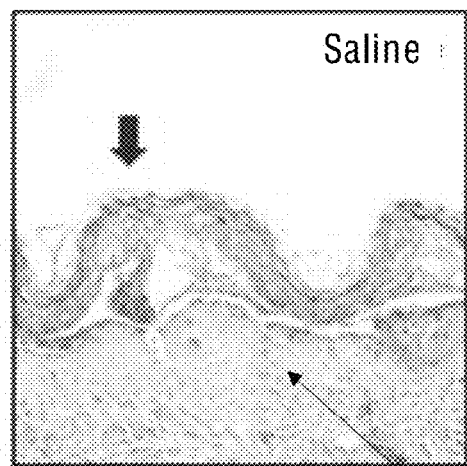
FIGS. 6a-6c show that re-epithelisation following burn is catalysed by copper ions. Burned skin treated or not with copper ions (0.02 µM and 1 µM) were harvested after 12 days, sectioned and stained with H&E. Enlarge boxes focus on the site of re-epithelisation. Dark arrows indicate detached dead epidermis. Beginning of epithelia regeneration (grey arrows) is seen upon treatment with copper ions, but not in the Burn Control section.
Figure 6A:
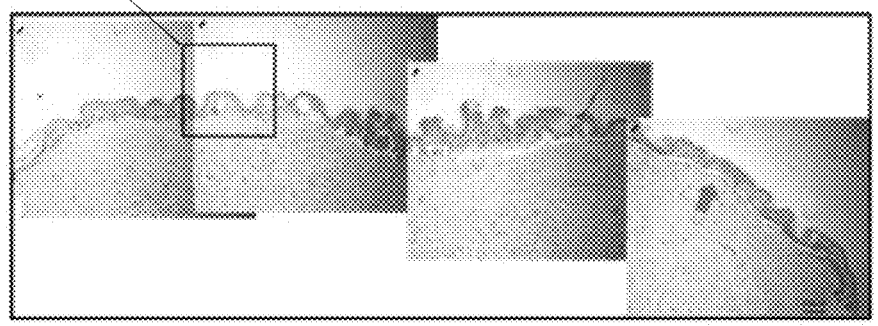
Figure 6B:
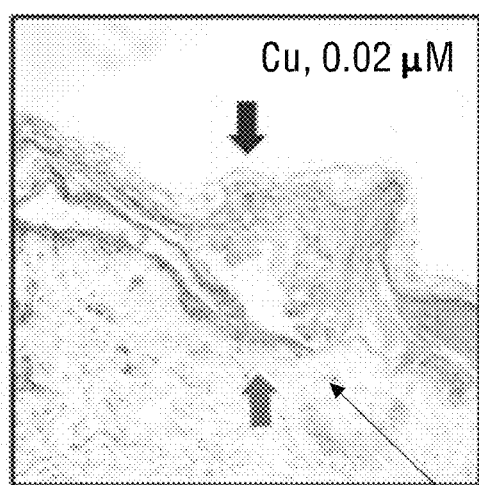
Figure 6B:
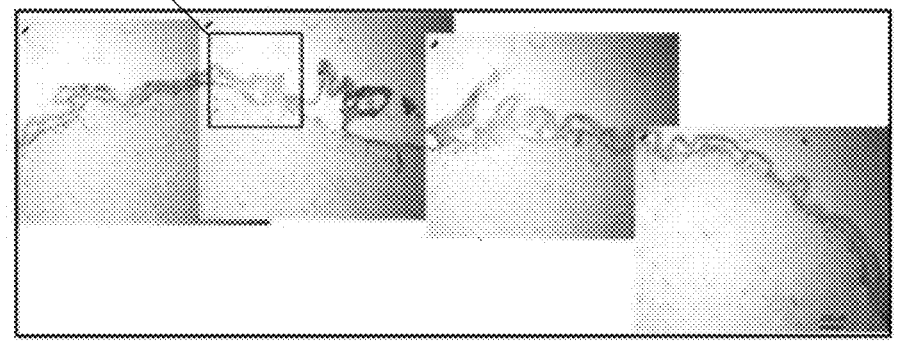
Figure 6C:
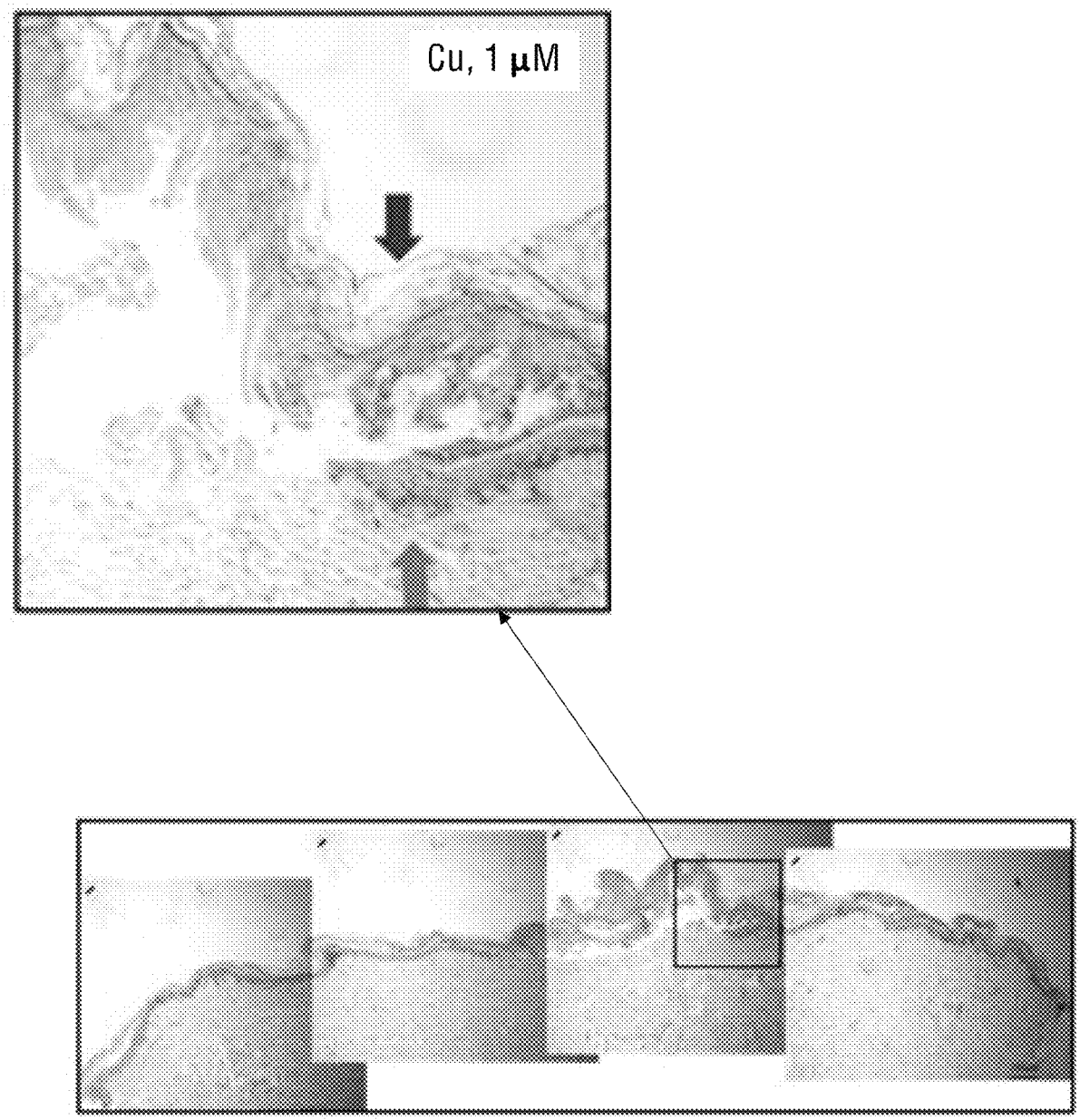

Examination of tissue formation was performed on day 12 and 27. Sections of Normal and Burned skin, treated or not with copper ions were stained with H&E and Masson's trichrome staining respectively. FIGS. 6a-6c show full length images of sections stained with H&E.

In FIG. 6a, upon burn, the damage of the burn is observed in the center of the tissue, where the epidermal layer is absent and old, dead epidermis is detached above (dark purple arrows). Additionally, newer separation of the epidermis from the dermis is observed further from the burn area (orange arrow) as a continuous damage. When the burns were treated with 0.02 µM or 1 µM, copper ions then were less detached of the epidermal tissue from the dermis (see FIGS. 6b and 6c). Higher magnification (enlarge boxes) enables detecting newly formed epithelia (leading epithelial tongue, grey arrows) at the edges of the epidermal detachment. To strengthen these results, sections were immune-stained against Ki67 to detect proliferating cells at the site of re-epithelisation.

Figure 7:
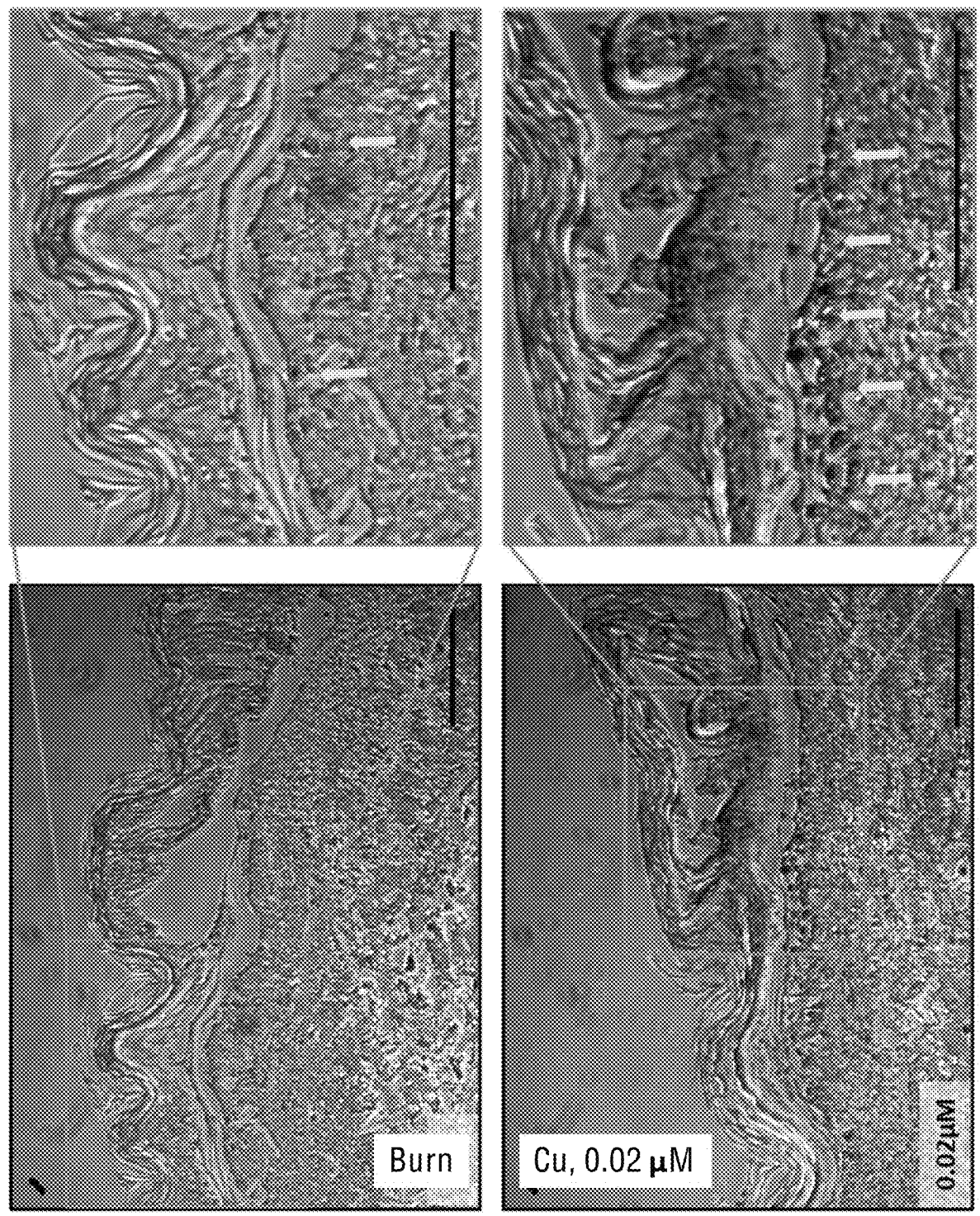
FIG. 7 shows keratinocytes proliferation at the re-epithelisation area. Skin pieces fixed after 12 days were labelled with anti-ki67 and secondary HRP-conjugated antibody. Counterstain was performed with haematoxylin. Upon burn, newly proliferating cells, stained with Ki67 (brown nuclei), indicated by yellow arrows, are significantly more common in the copper treated explants.

When burned skin was treated with 0.02 µM of copper ions, a significantly higher amount of Ki67 stained cells compared to control was observed (see FIG. 7). Burned skin explants were harvested after 27 days, sectioned and stained with Masson's trichrome staining which enables to detect both epidermal and dermal changes by staining cells in red and collagen fibers in blue.

Thus, in above experiments, the impact of thermal burns on the skin tissue has been extensively investigated due to its high relevance to public health. In these experiments, evidence has been shown that supports the beneficial role of local copper administration for the treatment of thermal burns with emphasis on the reduction of burn area at early periods of the healing process and the accompanying inflammatory process. Collectively, the present experiments lay the ground for clinical implications of copper impregnated fabrics for the treatment of thermal burns.

The present invention thus provides the healing process of thermal burns in ex-vivo human skin model upon treatment with copper ions, from two different sources, by using various healing markers by means of histology and immunohistochemistry methods, as well as cytokine secretion to the growth media and ECM remodeling.

As shown in the present invention, post burning, monitoring of the skin pieces was performed kinetically. During the early days following burn infliction, at the inflammatory stage, an elevated secretion of the pro-inflammatory cytokines IL-6 and IL-8 was detected. Although in this experimental system, the skin pieces are detached from an organism and the vascular system and, therefore, cannot simulate an inflammatory response involving an oscillation of immune cells to the wound area, it allows detecting local responses of the burn microenvironment.

The thermal burn caused an increased secretion of IL-6 and IL-8 to the growth media compared to normal skin. At Day 1 following the burn the levels of IL-6 were dramatically elevated in the Burn Controls but not in the copper ion treated samples. The IL-6 secretion decreased to basal level in all samples on day 6. The secretion of IL-8 immediately after burning in the saline treated samples was biphasic-being first reduced by ~30% on Day 1 and increased by ~35% at Day 4 post burning. Interestingly, the copper ions treated burned samples behaved as the saline treated samples with the exception of Day 4, in which IL-8 secretion was significantly lower in the copper treated samples than in saline (control) treated burn samples.

Secretion of TGF-β, which is associated with processes of wound healing by stimulating fibroblasts and infiltrated immune cells was, as expected, elevated in response to the burn damage. However, its level was dramatically inhibited by copper ions on Day 4, returning to normal levels on Day 6 and onwards. The reduced secretion of TGF-shortly after burning may have contributed significantly to the reduced inflammatory response and deterioration especially of the zone of stasis, preventing the increase in the wound size, which occurred in the saline treated burn samples only. The increased secretion of TGF-β on Day 6 in the copper treated burn samples may be important, as TGF-β also plays a critical role at advanced stages of wound healing in the context of tissue differentiation, remodeling and scar formation. Indeed, earlier proliferation of keratinocytes and epithelisation in the copper ion treated samples occurred, as seen in FIGS. 4a-4c, 6a-6c and 7.

Taken together, the experimental results clearly support the present invention and suggest the beneficial role for copper ions in preventing scarring or at least the formation of hypertrophic scarring by copper treatment.

Ex-vivo treatments with copper ions extracted from copper oxide-impregnated dressings on skin resulted in increased expression of collagen and elastin as well as an increase in the amount of their fibers in the dermal tissue. Also, in the copper treated burned samples, an increase in the amount of collagen fibers than in the saline-treated control group was found, as seen in the dermal layer in FIG. 4c.

In the present invention, cuprous oxide ($Cu_2O$) or copper iodide (CuI) impregnated fabrics were used as a source for copper ions. These fabrics are however exemplary and are not limited to $Cu_2O$ or CuI. Woven or non-woven fabric, a foam, a knit fabric, or any type of fabric that is used to make wound dressings, plasters, gauze or the like, containing other water-soluble or water-insoluble copper compounds can be used in the present invention. Topical application of the ions had reduced dramatically inflammation manifestations and prevented the increase in burn size that occurs after the initial damage. No significant differences in regards to the source of the copper ions, i.e. from cuprous oxide or copper iodide impregnated fabrics, were found in the present invention. Although burn size at the end of the experiment was not massively improved, due to limitations of the experimental model, this ameliorating effect can have long term implications, such as healthier scarring.

The ex-vivo model allows to detect local responses of the skin microenvironment that do not include infiltration of immune cells to the burn area. Further long-term clinical investigation is of need to validate the feasibility of copper-containing wound dressing for the treatment of burns.

The invention claimed is:

1. A method for reduction and prevention of formation of a zone of stasis in a burnt skin area:
    comprising applying a material impregnated or coated with about 0.1-10% w/w water-insoluble copper particles to said burnt skin area,
    wherein said material is a woven or non-woven fabric, a foam, a knit fabric, or fabric used in manufacturing medical items, or said material is in a form of a polymeric film, fibre, filament or sheath,
    wherein said water-insoluble copper particles are cuprous iodide (CuI), cuprous oxide ($Cu_2O$), or cupric oxide (CuO) particles, or combinations thereof, and
    wherein said material is applied immediately after the skin burn before the inflammatory natural skin response occurs.

2. The method of claim 1, wherein said material is a woven fabric impregnated or coated with approximately 0.1-10% w/w cuprous iodide (CuI) particles.

3. The method of claim 1, wherein said material is a sterile wound dressing impregnated or coated with approximately 0.1-10% w/w $Cu_2O$ particles.

4. The method of claim 1, wherein said polymeric film comprises at least one polymer selected from polyester, polypropylene, polyethylene, Nylon 66, Nylon 6, polyamide and polyurethane.

5. The method of claim 4, wherein said polymeric material comprises water-insoluble particles of copper compounds in a powdered form, embedded directly inside said film, fibre, filament or sheath, wherein a portion of said particles being exposed and protruding from the surface of the film, fibre, filament or sheath.

6. The method of claim 1, wherein said material is fabric wound dressings, plasters, or gauze.

* * * * *